United States Patent [19]

Loev et al.

[11] Patent Number: 4,500,527

[45] Date of Patent: Feb. 19, 1985

[54] ANTIHYPERTENSIVE 4[(3-ALKYLAMINO-2-HYDROXYPROPYL)-OXYIMINOMETHYL PHENYL]-1,4-DIHYDROPYRIDINES

[75] Inventors: Bernard Loev, Scarsdale, N.Y.; James R. Shroff, Riverside, Conn.; Rohit Desai, Millwood, N.Y.

[73] Assignee: USV Pharmaceutical Corporation, Tarrytown, N.Y.

[21] Appl. No.: 506,732

[22] Filed: Jun. 22, 1983

[51] Int. Cl.³ .................. A61K 31/54; A61K 31/455; C07D 211/82; C07D 417/00
[52] U.S. Cl. .................... 514/223; 514/236; 514/266; 514/341; 514/343; 544/405; 544/277; 544/46; 544/102; 544/124; 546/321; 546/281; 546/278; 546/279; 546/273; 546/272; 546/271; 546/275; 514/252
[58] Field of Search ............... 546/321, 281, 278, 279, 546/273, 272, 271, 275; 424/266, 250, 247, 248.55, 253; 544/405, 277, 124, 46, 102

[56] References Cited

U.S. PATENT DOCUMENTS 3,959,296 5/1976 Bossert et al. .................. 424/266

Primary Examiner—Henry R. Jiles
Assistant Examiner—Dale A. Bjorkman

[57] ABSTRACT

Unsaturated heterocyclic dihydropyridines of the formula:

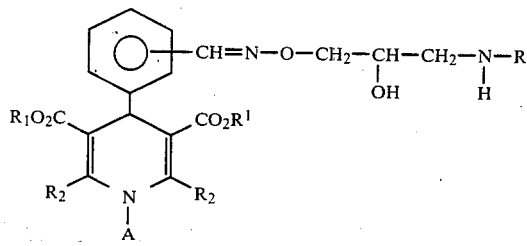

wherein the substituents defined herein have been found to have useful antihypertensive activity.

12 Claims, No Drawings

ANTIHYPERTENSIVE 4[(3-ALKYLAMINO-2-HYDROXYPROPYL)-OXYIMINOMETHYL PHENYL]-1,4-DIHYDROPYRIDINES

This invention relates to new anti-hypertensive agents and more particularly to certain substituted 1,4-dihydropyridines possessing useful pharmaceutical activity.

The new compounds of the present invention are unsaturated heterocyclic dihydropyridines of the formula:

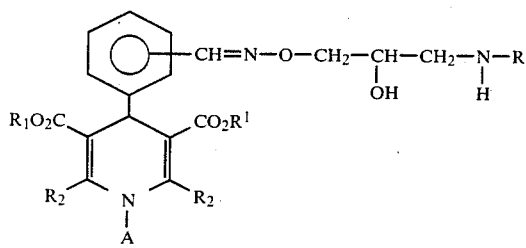

wherein

R is alkyl, preferably a straight or branched alkyl having 1-10 carbon atoms;

A is H, alkyl having 1-10 carbon atoms, or X;

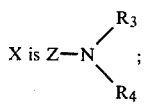

Z is alkylene containing 1 to about 5 carbon atoms in the principal chain;

$R_3$ and $R_4$ together with the nitrogen to which they are attached may form an unsaturated heterocyclic compound, or a heterocyclic compound containing an additional hetero atom such as one of the following: pyrrolyl, imidazolyl, pyrazolyl, dihydropyrazinyl, indolyl, isoindolyl, purinyl, carbazolyl, β-carbolinyl, phenthiazinyl, phenoxazinyl, pyrrolinyl, pyrazolinyl, (o) or (p) isoxazinyl, imidazolinyl, or morpholino;

$R_3$ and $R_4$ also can independently be H, alkyl, phenyl, cycloalkyl, hydroxyalkyl, alkoxyalkyl, or phenylalkyl;

each $R_1$ is independently H, lower alkyl, or alkoxyalkyl;

each $R_2$ is independently lower alkyl, formyl, CN, $CH_2OH$, dialkylaminoalkyl, aryl (substituted and unsubstituted), aryl lower alkylene, heteroaryl, or

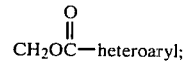

and pharmaceutically acceptable salts thereof.

It is preferred that when $R_3$ and $R_4$ are alkyl, cycloalkyl, hydroxyalkyl, alkoxyalkyl or phenylalkyl, each contains 2 to 4 carbon atoms in the alkyl group.

It is preferred that $R_1$ be lower alkyl or alkoxyalkyl and $R_2$ be lower alkyl, wherein alkyl contains 1 to 4 carbon atoms.

It is preferred that R be a branched alkyl of 4-10 carbon atoms, for example, $C(CH_3)_3$.

Particularly preferred compounds are when $R_1$ is $C_1$-$C_4$ alkyl, $R_2$ is $C_1$-$C_4$ alkyl, A is H, $C_1$-$C_4$ alkyl, or morpholinoethyl, and

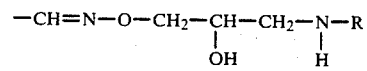

is at the 4 position.

The compounds of the present invention have pharmacological activity. The compounds are antihypertensive and may be useful β-adrenergic blocking agents. The compounds are thus useful to treat hypertension in animals, especially humans.

In treating hypertension in human patients, the daily dosage will range from about 1 mg to about 1000 mg; preferably from about 10 mg to about 800 mg daily; and more preferably from about 10 mg to about 800 mg daily; and more preferably from about 50 mg to about 500 mg per day.

The compound may be administered by any convenient route e.g. orally, parenterally, intramuscularly and the like using pharmaceutical compositions in a suitable dosage form e.g. tablets, elixirs, solutions or suspensions for oral administration and in sterile solutions for parenteral administration, and the like. These pharmaceutical compositions are prepared using conventional preparation procedures and can contain pharmaceutically acceptable compounding ingredients i.e. diluents, carriers, where required. These pharmaceutical compositions comprise another embodiment of the present invention.

Compounds of the invention can be prepared by art-recognized procedures from known similar starting compounds as described in U.S. Pat. No. 4,258,042 which is included by reference herein. In this patent the starting material is a substituted benzaldehyde. To obtain compounds of the present invention, the starting material is a cyanobenzaldehyde, which is then reacted as exemplified in Example 1.

A general scheme is as follows:

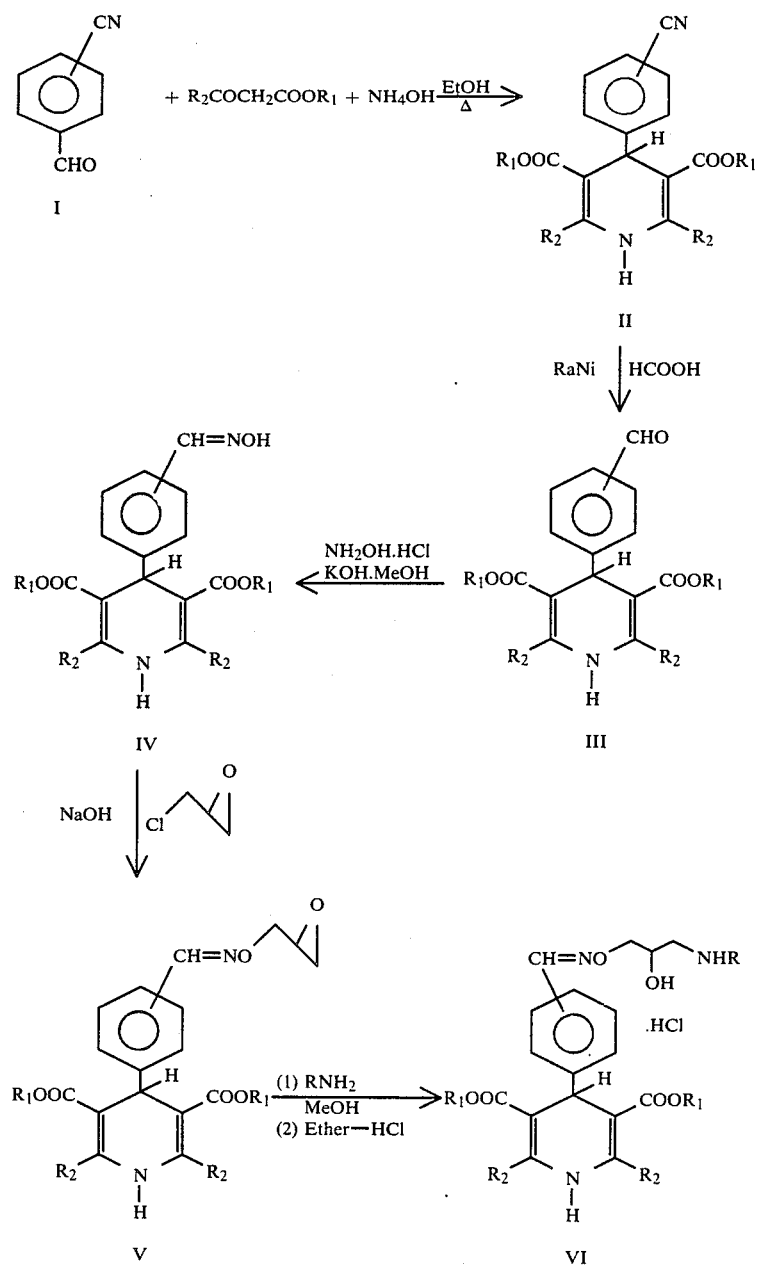

Employing similar procedures, a variety of new compounds of the following formula can be prepared:

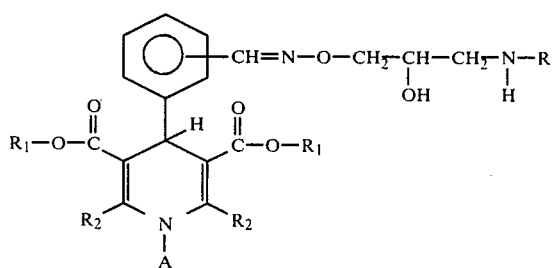

(a) wherein $$-CH=N-O-CH_2-CH-CH_2-N-R$$
$$\phantom{-CH=N-O-CH_2-}|\phantom{CH-CH_2-}|$$
$$\phantom{-CH=N-O-CH_2-}OH\phantom{CH_2-}H$$

is at the 4 position;

| A | $R_1$ | $R_2$ | R |
|---|---|---|---|
| H | $CH_3$ | $CH_3$ | $CH_3$ |
| H | $C_2H_5$ | $C_2H_5$ | $CH_2CH_3$ |
| H | $C_2H_5$ | $CH_3$ | $CH_2CH_2CH_3$ |
| H | $CH_3$ | $C_2H_5$ | $(CH_2)_4CH_3$ |
| $CH_3$ | $C_2H_5$ | $CH_3$ | $C(CH_3)_3$ |
| $CH_2CH_3$ | $CH_3$ | $C_2H_5$ | $CH_2C(CH_3)_3$ |
| H | $C_2H_5$ | $CH_3$ | $C(CH_3)_3$ |

(b) wherein

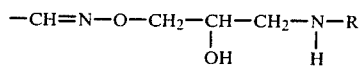

is at the 2 position;

| A | $R_1$ | $R_2$ | R |
|---|---|---|---|
| H | $CH_3$ | $CH_3$ | $CH_3$ |
| H | $C_2H_5$ | $C_2H_5$ | $CH_2CH_3$ |
| H | $C_2H_5$ | $CH_3$ | $CH_2CH_2CH_3$ |
| H | $CH_3$ | $C_2H_5$ | $(CH_2)_4CH_3$ |
| $CH_2CH_3$ | $C_2H_5$ | $CH_3$ | $C(CH_3)_3$ |
| $CH_2CH_3$ | $CH_3$ | $C_2H_5$ | $CH_2C(CH_3)_3$ |
| H | $C_2H_5$ | $CH_3$ | $C(CH_3)_3$ |

(c) wherein

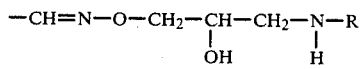

is at the 3 position;

| A | $R_1$ | $R_2$ | R |
|---|---|---|---|
| H | $CH_3$ | $CH_3$ | $CH_3$ |
| H | $C_2H_5$ | $C_2H_5$ | $CH_2CH_3$ |
| H | $C_2H_5$ | $CH_3$ | $CH_2CH_2CH_3$ |
| H | $CH_3$ | $C_2H_5$ | $(CH_2)_4CH_3$ |
| $CH_2CH_3$ | $C_2H_5$ | $CH_3$ | $C(CH_3)_3$ |
| $CH_2CH_3$ | $CH_3$ | $C_2H_5$ | $CH_2C(CH_3)_3$ |
| H | $C_2H_5$ | $CH_3$ | $C(CH_3)_3$ |

(d) wherein

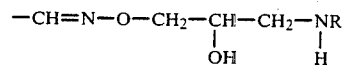

is at the 4 position and

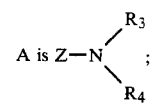

TABLE I

| Z | $R_3$ | $R_4$ | $R_2$ | $R_1$ | R |
|---|---|---|---|---|---|
| $CH_2CH_2$ | pyrazolyl | | $C_2H_5$ | $CH_3$ | $CH_3$ |
| $CH_2CH_2$ | pyrrolyl | | $CH_3$ | $CH_3$ | $C_2H_5$ |
| $CH_2CH_2$ | pyrazolyl | | $CH_3$ | $CH_3$ | $C(CH_3)_3$ |
| $CH_2CH_2$ | pyrrolyl | | $C_2H_5$ | $CH_3$ | $C_5H_{11}$ |
| $CH_2CH_2$ | pyrazolyl | | $C_2H_5$ | $CH_3$ | $C_{10}H_{21}$ |
| $CH_2CH_2$ | imidazolyl | | $CH_3$ | $C_2H_5$ | $C(CH_3)_3$ |
| $CH_2CH_2$ | dihydropyrazinyl | | $CH_3$ | $C_2H_5$ | $CH_2C(CH_3)_3$ |
| $CH_2CH_2$ | indolyl | | $CH_3$ | $C_2H_5$ | $CH_3$ |
| $CH_2CH_2$ | Isoindolyl | | $CH_3$ | $C_2H_5$ | $C_2H_5$ |
| $CH_2CH_2$ | purinyl | | $CH_3$ | $C_2H_5$ | $C(CH_3)_3$ |
| $CH_2CH_2$ | carbazolyl | | $CH_3$ | $C_2H_5$ | $C(CH_3)_3$ |
| $CH_2CH_2$ | phenthiazinyl | | $CH_3$ | $C_2H_5$ | $CH_3$ |
| $CH_2CH_2$ | phenoxazinyl | | $CH_3$ | $C_2H_5$ | $C_2H_5$ |
| $CH_2CH_2$ | pyrrolinyl | | $CH_3$ | $C_2H_5$ | $C(CH_3)_3$ |
| $CH_2CH_2$ | pyrazolinyl | | $CH_3$ | $C_2H_5$ | $C_3H_5$ |
| $CH_2CH_2$ | imidazolinyl | | $CH_3$ | $C_2H_5$ | $C_4H_9$ |
| $CH_2CH_2$ | (o)-isoxazinyl | | $CH_3$ | $C_2H_5$ | $C_5H_{11}$ |
| $CH_2CH_2$ | (p)-isoxazinyl | | $CH_3$ | $C_2H_5$ | $C_6H_{13}$ |
| $CH_2CH_2$ | purinyl | | $CH_3$ | $C_2H_5$ | $C_7H_{15}$ |
| $CH_2CH_2$ | isoindolyl | | $CH_3$ | $C_2H_5$ | $C_8H_{17}$ |
| $CH_2CH_2$ | H | $CH_3$ | $CH_3$ | $C_2H_5$ | $CH_3$ |
| $CH_2CH_2$ | $CH_3$ | $CH_3$ | $CH_3$ | $C_2H_5$ | $C_2H_5$ |
| $CH_2CH_2$ | $CH_2CH_3$ | $CH_3$ | $CH_3$ | $C_2H_5$ | $C(CH_3)_3$ |
| $CH_2CH_2$ | $C_3H_9$ | $CH_3$ | $CH_3$ | $C_2H_5$ | $C_5H_{11}$ |
| $CH_2CH_2$ | cyclopentyl | $CH_3$ | $CH_3$ | $C_2H_5$ | $C_3H_7$ |
| $CH_2CH_2$ | $HOCH_2$ | $CH_3$ | $CH_3$ | $C_2H_5$ | $C_4H_9$ |
| $CH_2CH_2$ | $CH_3OCH_2$ | $CH_3$ | $CH_3$ | $C_2H_5$ | $C_5H_{11}$ |
| $CH_2CH_2$ | $CH_3OCH_2$ | $CH_2OH$ | $CH_3$ | $C_2H_5$ | $C_6H_{13}$ |
| $CH_2CH_2$ | cyclopentyl | $CH_3OCH_2$ | $CH_3$ | $C_2H_5$ | $C_7H_{15}$ |
| $CH_2CH_2$ | cyclopentyl | $CH_2OH$ | $CH_3$ | $C_2H_5$ | $C_8H_{17}$ |
| $CH_2CH_2$ | cyclopentyl | H | $CH_3$ | $C_2H_5$ | $C_9H_{19}$ |
| $CH_2CH_2$ | $HOCH_2$ | H | $CH_3$ | $C_2H_5$ | $C_{10}H_{21}$ |
| $CH_2CH_2$ | $CH_3OCH_2$ | H | $CH_3$ | $C_2H_5$ | $CH_2C(CH_3)_3$ |
| $CH_2CH_2$ | thiazine | | $CH_3$ | $CH_3$ | $C_2H_5C(CH_3)_3$ |
| $CH_2CH_2$ | thiazine | | $CH_3$ | $CH_3$ | $C(CH_2)_2-CH_3$ |
| $CH_2CH_2$ | thiazine | | $CH_3$ | $CH_3$ | $CH_2C(CH_2)_2CH_3$ |
| $CH_2CH_2$ | morpholino | | $C_2H_5$ | $CH_3$ | $C(CH_3)_3$ |
| $CH_2CH_2$ | morpholino | | $C_2H_5$ | $CH_3$ | $CH_2C(CH_3)_3$ |
| $CH_2CH_2$ | morpholino | | $C_2H_5$ | $CH_3$ | $C_2H_5$ |
| $CHCH_3$ | pyrrolyl | | $CH_3$ | $C_2H_5$ | $C(CH_3)_3$ |
| $CHCH_3$ | imidazolyl | | $CH_3$ | $C_2H_5$ | $C(CH_3)_3$ |
| $CH_2CH_2$ | pyrazolyl | | $CH_3$ | $C_2H_5$ | $C(CH_3)_3$ |
| $CH(CH_3)CH_2$ | dihydropyrazinyl | | $C_2H_5$ | $C_2H_5$ | $C(CH_3)_3$ |
| $CH_2CH_2$ | indolyl | | $CH_3$ | $i-C_3H_7$ | $C(CH_3)_3$ |
| $CH_2CH_2$ | isoindolyl | | $CH_3$ | $C_2H_5$ | $C(CH_3)_3$ |
| $CH_2CH_2$ | carbazolyl | | $C_3H_7$ | $CH_3$ | $C(CH_3)_3$ |
| $CH(CH_3)$ | β-carbolinyl | | $C_4H_9$ | $C_2H_5$ | $C(CH_3)_3$ |
| $(CH_2)_3$ | phenthiazinyl | | $C_6H_{13}$ | $C_2H_5$ | $C(CH_3)_3$ |
| $CH_2CH_2$ | phenoxozinyl | | $i-C_4H_9$ | $CH_3$ | $C(CH_3)_3$ |
| $(CH_2)_5$ | pyrazolinyl | | $CH_3$ | $C_2H_5$ | $C(CH_3)_3$ |

TABLE I-continued

| Z | R₃ N R₄ | R₂ | R₁ | R |
|---|---|---|---|---|
| $CH_2CH_2$ | (o) isoxazinyl | $CH_3$ | $C_2H_5$ | $C(CH_3)_3$ |
| $CH_2CH_2$ | (p) isoxazinyl | $CH_3$ | $C_2H_5$ | $C(CH_3)_3$ |
| $CH(CH_3)CH_2$ | imidazolinyl | $CH_3$ | $C_2H_5$ | $C(CH_3)_3$ |

EXAMPLE 1

A. Diethyl 1,4-dihydro-4-(4-cyanophenyl)-2,6-dimethyl-3,5-pyridinedicarboxylate p-Cyanobenzaldehyde (45.9 gms; 0.35 mole), acetoacetic ester (91.0 gms; 89.1 ml; 0.7 mole) and 36.4 ml ammonium hydroxide were combined in 200 ml ethanol and refluxed for a period of 21 hours. The yellow solution was poured into crushed ice and the tacky yellow solid recrystallized from 2-propanol to yield 79.5 gms (64.2%) of the dihydropyridine, mp 155°–160° C.

B. Diethyl 1,4-dihydro-4-(4-benzaldehydo)-2,6-dimethyl-3,5-pyridinedicarboxylate The product of A (35.5 gms; 0.1 mole), 600 ml 50% HCOOH and 40 gms of Raney Nickel were combined and refluxed for a period of 6 hours, and then allowed to cool. The cooled green solution was vacuum filtered and the residue was washed with chloroform. The aqueous layer of the filtrate was extracted with chloroform and the combined organic solution was washed twice with 0.5N aqueous sodium bicarbonate, dried (anhydrous sodium sulfate) and concentrated to a brown oil weighing 17.0 gm. Recrystallization from toluene yielded 11.0 gms (32.4%) of yellow crystals, mp 148°–149° C.

C. Diethyl 1,4-dihydro-4-[4-(hydroxyimino)methyl]-2,6-dimethyl-3,5-pyridinedicarboxylate The product of B (5.3 gms; 0.015 mole) was dissolved in 75 ml of methanol with warming and allowed to cool to room temperature. A solution of hydroxylamine hydrochloride (2.1 gms; 0.045 mole) (50%) was added to the dihydropyridine. Immediate precipitation began and the reaction mixture was stirred for a period of 72 hours. The reaction mixture was vacuum filtered and the organic filtrate concentrated to a small volume. The orange pasty material was dissolved in chloroform and the chloroform layer washed with water, dried (anh. Na₂SO₄), and the solvent removed to yield a yellow pasty material. Crystallization from 2-propanol afforded 3.5 gms of material, mp 176°–179° C.

D. 4-[4-[[3-(1,1 Dimethylethyl)amino-2-hydroxypropoxyimino]methyl]phenyl]-1,4-dihydro-2,6-dimethyl-3,5-pyridine carboxylic acid diethyl ester hydrochloride The product of C (3.7 gms; 0.01 mole), 1 ml 50% sodium hydroxide, and 25 ml epichlorohydrin were allowed to stir at room temperature for a period of 48 hours. The reaction mixture was diluted with chloroform, the chloroform layer washed with water, dried (anh. Na₂SO₄) and concentrated to yield 4.0 gms. of the crude epoxide. The crude epoxide and t-butylamine (3 ml) were combined in 50 ml methanol and the reaction mixture refluxed for a period of 3 hours, then concentrated to yield a brown paste. The paste was washed twice with ether, leaving a yellow semi-solid. Ether-HCl was added to the ether and the salt extracted out with water. The aqueous phase was basified with 1N NaOH and extracted into ether, which was washed with water, dried (anh. Na₂SO₄) and concentrated to yield 2.7 gms. of material. Extracted with ether and Ether-HCl added to form the hydrochloride salt. Recrystallization from acetonitrile afforded 1.25 gms of off-white crystals, mp 203°–204° C.

The compound of Example 1 was biologically tested, with results of the tests as follows:

30 mg/kg of the compound was administered intraperitoneally to spontaneously hypertensive rats (SHR). The SHR's arterial pressure decreased 30–35% for 14–24 hours. The test was as described in Technique For Prolonged Continuous Recording of Blood Pressures of Unrestricted Rats, Cardiovascular Research, Vol. 6, pp. 319–24, 1972.

The compounds were also administered to sodium depleted SHR in the same dose and same route. This test showed a decrease in arterial pressure by 29–35%.

EXAMPLE 2

4-[4-[[3-(-(1,1-Dimethylethyl)amino-2-hydroxypropoxyimino]methyl]phenyl]1-(2-morpholinoethyl)1,4-dihydro-2,6-dimethyl-3,5-pyridine carboxylic acid diethyl ester hydrochloride To a slurry of sodium hydride (0.5 gms; 0.01 mol; 50:50 oil dispersion) in dry distilled DMF (25 ml) under N₂ atmosphere is added a solution of diethyl 4-[4-(epoxypropoxyiminomethyl)phenyl]-1,4-dihydro-2,6-dimethyl-3,5-pyridinedicarboxylate (4.0 gms; 0.01 mol) in DMF (100 ml). After hydrogen bubbling ceases, the reaction mixture is warmed on a water bath for ½ hour and a toluene solution (100 ml) of N-(2-chloroethyl)-morpholine (1.6 gms; 0.01 mol) is added dropwise. The reaction mixture is stirred at 110°–115° C. for 4 hours. The reaction mixture is cooled, vacuum filtered to remove NaCl, and the filtrate concentrated in vacuo. The residue and t-butylamine (2–3 ml) is combined in 50 ml methanol and the reaction mixture is refluxed for a period of 3 hours, then is concentrated to yield a pasty material. Ether-HCl is added to the ether solution of the pasty material to afford the hydrochloride salt.

We claim:
1. A compound of the formula

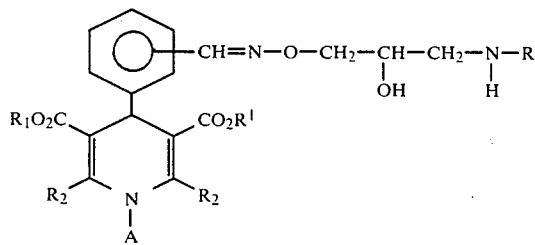

wherein
R is $C_1$-$C_{10}$ alkyl,
each $R_1$ is independently H, $C_1$-$C_4$ alkyl, or $C_1$-$C_4$ alkoxy $C_1$-$C_4$ alkyl;
each $R_2$ is independently H, $C_1$-$C_4$ alkyl, formyl, CN, $CH_2OH$, or di $C_1$-$C_4$ alkylamino $C_1$-$C_4$ alkyl;
A is H, $C_1$-$C_{10}$ alkyl, or X;
X is

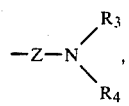

Z is $C_1$-$C_{15}$ alkylene;
$R_3$ and $R_4$ are independently H, $C_1$-$C_4$ alkyl, $C_3$-$C_4$ cycloalkyl, hydroxy $C_1$-$C_4$ alkyl, $C_1$-$C_4$ alkoxy $C_1$-$C_4$ alkyl, or phenyl $C_1$-$C_4$ alkyl, or $R_3$ and $R_4$ together with the nitrogen to which they are attached form pyrrolyl, imidazolyl, pyrazolyl, dihydropyrazinyl, indolyl, isoindolyl, purinyl, carbazolyl, β-carbolinyl, phenthiazinyl, phenoxazinyl, pyrrolinyl, pyrazolinyl, (o) or (p) isoxazinyl, imidazolinyl, or morpholino; or a pharmaceutically acceptable salt thereof.

2. A compound of claim 1 wherein each $R_1$ is independently $C_1$-$C_4$ alkyl, or $C_1$-$C_4$ alkoxy $C_1$-$C_4$ alkyl, each $R_2$ is independently $C_1$-$C_4$ alkyl.

3. A compound of claim 1 wherein R is a branched alkyl of 3-10 carbon atoms.

4. A compound of claim 1 wherein

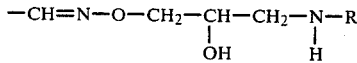

is at the 4 position.

5. A compound of claim 1 wherein

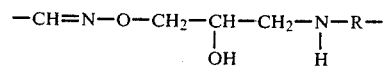

is at the 2 position.

6. A compound of claim 1 wherein

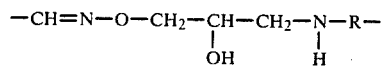

is at the 3 position.

7. A compound of claim 4 wherein $R_1$ is $C_1$-$C_4$ alkyl, $R_2$ is $C_1$-$C_4$ alkyl, A is H, $C_1$-$C_4$ alkyl or X, and X is

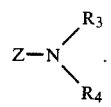

8. A compound of claim 7 wherein

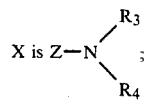

and Z is an alkylene containing $C_1$-$C_{15}$ atoms in the principal chain.

9. A compound of claim 4 wherein A is H, $C_1$-$C_4$ alkyl or morpholinoethyl.

10. Diethyl 4[4-(3-t-butylamino-2-hydroxypropyl)oxyiminomethyl]phenyl]-1,4-dihydro-2,6-dimethyl-3,5-pyridinedicarboxylate and its salts.

11. A pharmaceutical dosage form for treating hypertension in mammals, said dosage form containing amount effective for treating hypertension of a compound of claim 1 and a pharmaceutically acceptable carrier.

12. A method for treating hypertension in mammals requiring said treatment, wherein the method comprises the administration of an effective amount of a compound of claim 1.

* * * * *